United States Patent [19]

Baker et al.

[11] Patent Number: 4,552,024
[45] Date of Patent: Nov. 12, 1985

[54] DEVICE FOR DIRECTLY ANALYZING STRENGTH OF CERAMIC TOOL BITS

[75] Inventors: Robert R. Baker; Richard L. Allor, both of Livonia, Mich.

[73] Assignee: Ford Motor Company, Dearborn, Mich.

[21] Appl. No.: 598,753

[22] Filed: Apr. 10, 1984

[51] Int. Cl.⁴ .............................................. G01N 3/08
[52] U.S. Cl. ......................................... 73/821; 73/852
[58] Field of Search .................. 73/821, 818, 852, 85, 73/81

[56] References Cited

U.S. PATENT DOCUMENTS 2,032,989  3/1936  Kenney et al. ........................ 73/852
3,874,228  4/1975  Fatt ....................................... 73/821

FOREIGN PATENT DOCUMENTS 129058  9/1959  U.S.S.R. ................................ 73/852

OTHER PUBLICATIONS

Greenbank et al., "Apparatus for Bending Crystals at Constant Strain Rate", J. Phys. E(GB), vol. 3, 11/70, pp. 949–950.

Primary Examiner—Anthony V. Ciarlante
Attorney, Agent, or Firm—Joseph W. Malleck; Roger L. May

[57] ABSTRACT

To induce fracture under test conditions for a tool bit configuration held in a laterally restrained condition, but with freedom to move up and down, a series of members (hardened steel ball bearings) are selected as to size, butted together, and constrained so that such members make tangential point contact with a constrained bit at locations close to the corners of one end surface supported on the members. When a centralized load is imposed on the opposite end surface of the bit, stress forces can be set up on the bit to result in a body bend fracture or an edge chip fracture, depending on how close the point contacts are to a curved sector. Each point contact is located along a radius bisecting a corner sector, the location being spaced from the sector a distance either (a) of at least one-half the sector radius, but within 0.01875–0.0312 inch, to induce edge chip fracture, or (b) of at least the sector radius, but no less than 0.0625 inch, to induce bend strength fracture.

8 Claims, 4 Drawing Figures

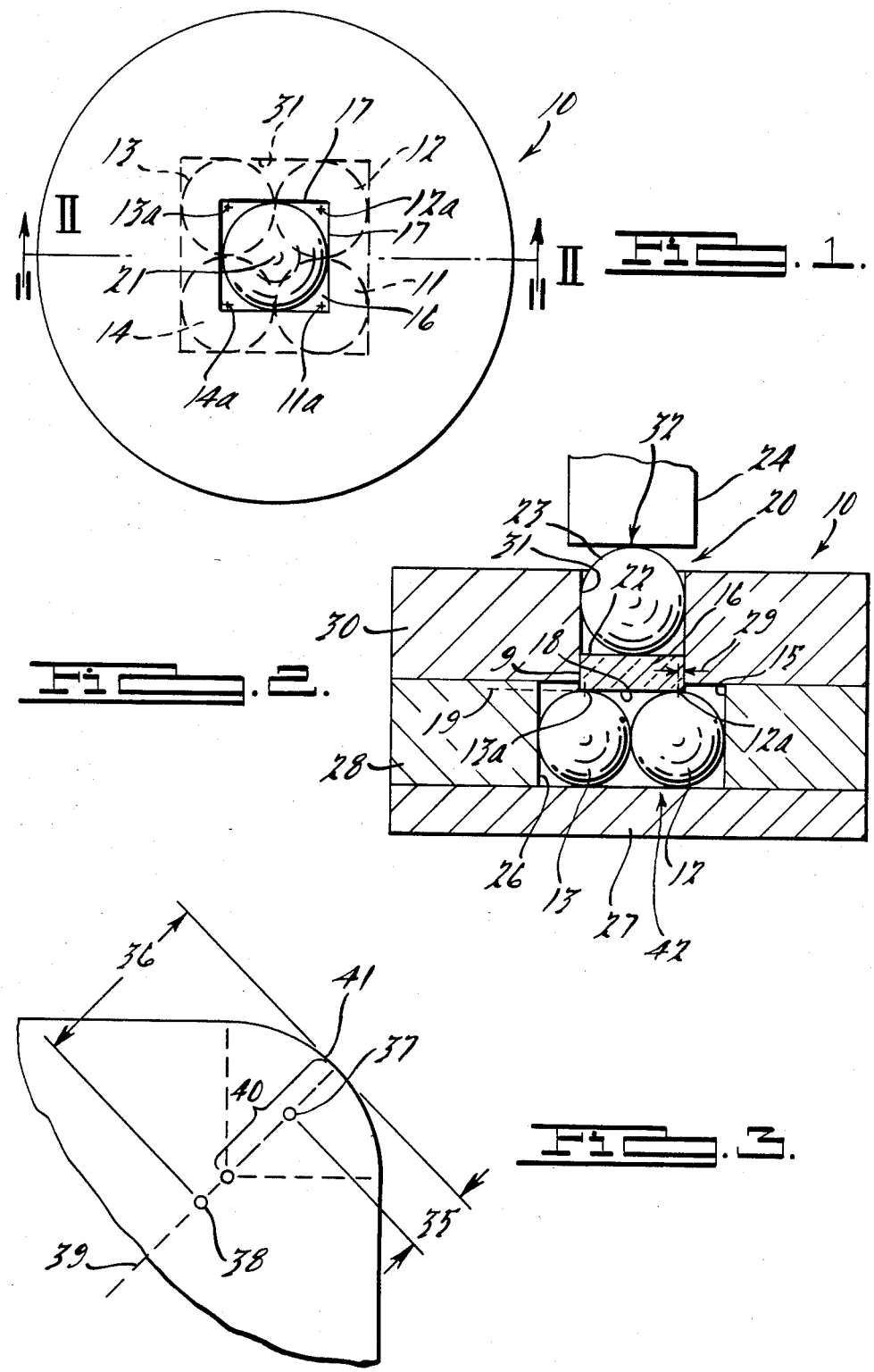

DEVICE FOR DIRECTLY ANALYZING STRENGTH OF CERAMIC TOOL BITS

TECHNICAL FIELD

This invention relates to a device for testing the edge chipping strength and mounting strength of prism shaped ceramic bodies.

BACKGROUND OF THE INVENTION AND PRIOR ART STATEMENT

Physical properties such as bend strength or degree of deflection for various cutting tool materials are usually tested by first making a separate test piece, of similar material, and placing the test piece on two fulcrum points or cylinders and applying a load intermediate to the fulcrum points (this is often referred to as a 3-point bend test and disclosed in U.S. Pat. Nos. 2,404,584 and 4,213,349). The test specimen must be sized to about $1/10 \times \frac{1}{8} \times 1\frac{1}{4}$ inches (see "Ceramic Cutting Tools Production, A Process Summary", by American Feldmuehle Corp., undated, page 2 and FIG. 4). In some cases the test piece may be placed in a 4-point bend test to analyze fracture strength. It should be emphasized that each of these methods requires the making of special specimens or test pieces to test the strength of the material and subject to uniaxial stress distribution. The specimens, being only a body of material similar to the product to be used, do not provide for direct testing of the product itself. Since such test specimens are ground by abrasive tools to the required shape, the ground specimen can never be identical to the product; grinding ensures that each specimen will be slightly different. Although the specimens are assumed to be identical in the prior art tests, for purposes of the strength tests they can never be truly identical. Grinding differences influence the accuracy of the test. It would be advantageous if the ceramic product to be used were to be directly tested not only for rupture strength but also for edge chip strength. Direct testing uses the greater mass of the product to give better probability of accurate strength values and responds to the peculiar grinding characteristics in the material and any inherent flaws. Tool bits have a greater mass than conventional test specimens and are relatively stout. Hence, testing tool bits presents special problems when attempting to obtain reliable test results. No device has been devised by the prior art to accomplish this.

SUMMARY OF THE INVENTION

The invention is a method and apparatus for directly testing the strength of a prism shaped cutting tool bit. Such bits have a shape defined by parallelogram sides bounded by opposed polygonal end surfaces greater in dimension than the height of any of the sides. The corners of the polygonal end surfaces are each defined by a curved sector of predetermined radius.

To induce fracture under test conditions for a grinding tool bit configuration held in a laterally restrained condition, a series of members are selected as to size, butted together, and constrained so that such members make tangential point contact with the bit at locations close to the corners of the one end surface supported on the members. Then, when a centralized load is imposed on the opposite end surface, stress forces can be set up in the bit to result in a body bend fracture or an edge chip fracture, depending on how close the point contacts are to a curved sector.

Preferably each point contact is located along a radius bisecting a corner sector, the location being spaced from the sector a distance either (a) of at least one-half the sector radius, but advantageously within 0.01875–0.0312 inch, to induce edge chip fracture, or (b) of at least the sector radius, but no less than 0.0625 inch, to induce bend strength fracture.

Advantageously, the bit may have four cornered end surfaces and the series of members may be comprised of four hardened ball bearings, each making point contact along diagonals of the end surface.

The apparatus for directly testing the strength of a prism shaped ceramic cutting tool bit, with a configuration as given above, comprises: (a) means providing three or more abutting and constrained curvilinear members, each stationed to make tangential point contact with one end surface of said bit when supportably located on said members, said members being sized to regulate the positioning of one contact each in close proximity to each curved sector of said one end surface; (b) means restraining said bit in said located position on said members; and (c) load applying means for applying a force to substantially the center of the opposite end surface, which force is effective to induce fracture in said tool bit.

SUMMARY OF THE DRAWINGS

FIG. 1 is a plan view of principal parts of a test apparatus embodying the principles of this invention;

FIG. 2 is a sectional view taken substantially along line 2—2 of FIG. 1, with a force applying piston added;

FIG. 3 is an enlarged plan view of one end surface of the tool bit under test, illustrating the relation between corner curved sectors and the tangential point contacts of a supporting member.

BEST MODE FOR CARRYING OUT THE INVENTION

Figure 4:
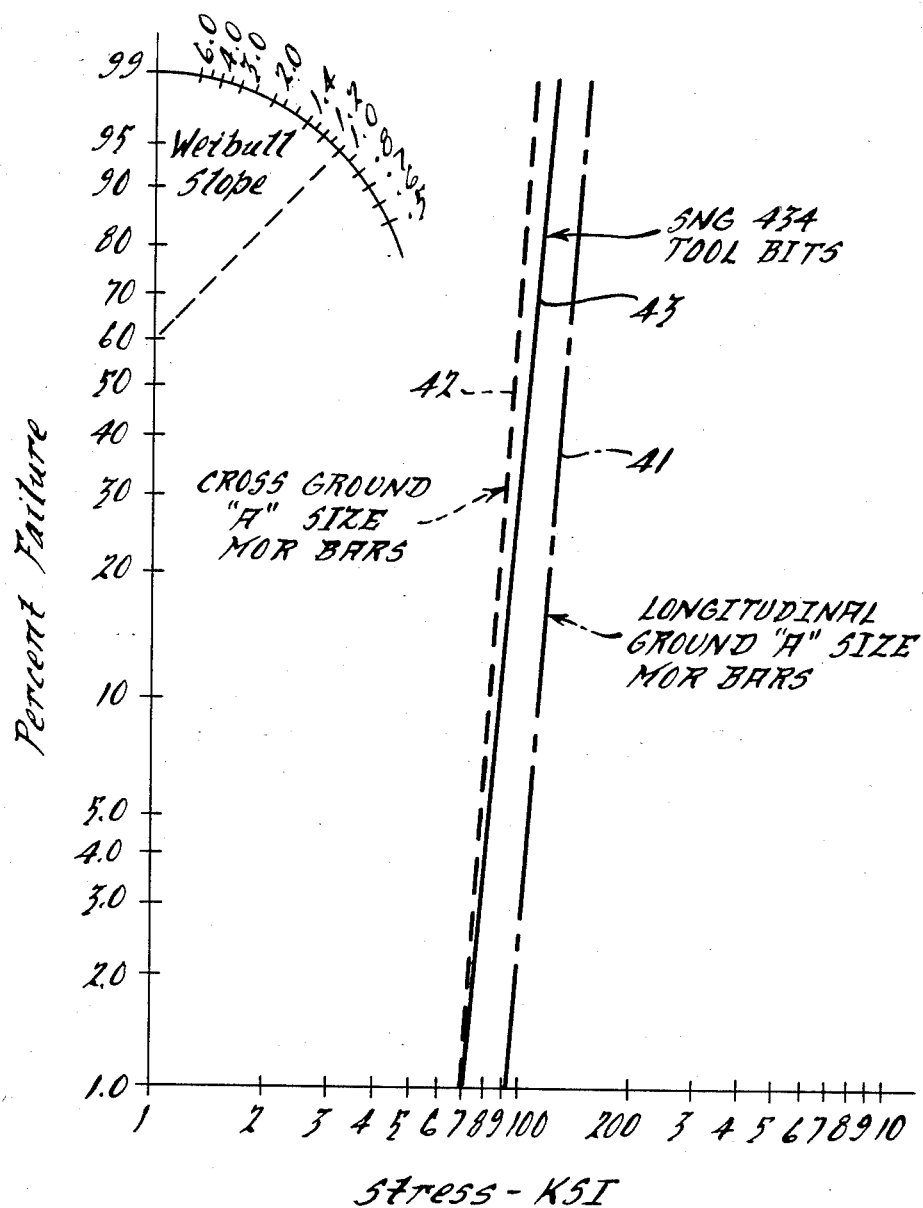
FIG. 4 is a graphical illustration of the percent failure plotted against stress for a large number of specimens subjected to either conventional test specimen testing or to direct bit testing under this invention.

A preferred apparatus for carrying out the invention is illustrated in FIGS. 1–3. A cutting tool bit 16, to be directly tested, has a ceramic prism shaped body. The prism has parallelogram sides 9 bounded by opposed polygonal end surfaces 18 and 22 defining edges 17. The end surfaces (here square polygons) are greater in dimension than the height of any side 9. The corners 41 of the polygonal end surfaces are each defined by a curved sector of a predetermined radius 40.

The testing apparatus 10 has means 42 providing three or more curvilinear members (here 11, 12, 13 and 14) which are abutting and constrained in a cavity 15 defined by plates 27 and 28. The members are stationed to make tangential point contact with one end surface 18 when the bit is supportably located on the members. The point contacts of the members are here identified as 11a, 12a, 13a and 14a.

The members are sized to regulate the positioning of one contact each in close proximity to each curved sector 41 of the end surface 18. As shown in FIG. 3, the degree of proximity will be determined by the type of strength test to be performed. To test for edge chip strength, the tangential point contacts (see contact 37 in FIG. 3 for illustration) are located along a radius, or here a diagonal 39, bisecting a corner sector 41. The location of the point contact 37 is spaced from the sector 41 a distance of about one-half the sector radius, but within the dimensional range of 0.01875–0.0312 inch. Consistently, the bit will chip at three of the four corners of a square bit; this does not mean the members (11–14) have been inaccurately located, it means that three of the members will determine an absolute plane for supporting the bit and the fourth contact will always be slightly out of such true theoretical plane.

To test for bend strength, the tangential point contacts (see contact 38 in FIG. 3 for illustration) are located along a radius, or here diagonal 39, bisecting a corner sector 41. The location of the point contact 38 is spaced from the sector 41 a distance of at least the sector radius 40 and no less than 0.0625 inches, whereby fracture will be induced as a break across the central region of the bit. The radius of the corner curvature is generally dictated by commercial standards and will generally fall into the range of 0.031–0.250.

The curvilinear members can be restrained in the desired position by means using a metal block or plate 28 having walls 26 defining an accurately dimensioned cavity 15 which in plan view is tangent to the outer periphery of all members (see FIG. 1). The cavity is closed at its bottom by a flat plate 27. The curvilinear members are preferably of equal radii facilitating tangential contact with a flat plane 19 and with a simple cubical cavity 15 defined by walls 26. The members are preferably highly polished metallic ball bearing spheroids having a dimensional accuracy of plus or minus 0.0001 inch and a surface finish of about 1.5 (arithmetic average) microinches and a hardness of at least 60 Rc.

A means 20 is employed to restrain the bit laterally for precise positioning over the curvilinear members to obtain the desired positioning of the tangential point contacts between end surface 18 and the members. Means 20 comprises a block 30 having interior walls 31 which snugly receives the bit for vertical movement. Means 20 also serves as part of the load applying means 32, the latter further comprising a spherical member 23 of a diameter to snugly fit between the interior walls 31 to be guided in the stroking movement as forced downwardly by piston or actuator 24. Means 32 should be effective to apply a load substantially at the center of end surface 22 to induce the desired fracture. This, of course, is made practical by (a) the use of the spherical member 23 which makes a tangential point contact with end surface 22 (b) walls 31 are substantially perpendicular to surface 22, and (c) member 23 is tangent to all the walls 31 and surface 22.

A preferred method for carrying out the invention comprises the following steps: (a) locating a series of contrained members (11, 12, 13, 14) selected as to size and butted together so that such members make tangential point contact with one bit end surface 18 supported on said members, the contacts being at locations in close proximity to the corners of the one end surface; (b) laterally restraining the bit supported on the members; and (c) applying a centralized load to the opposite end surface to induce stress in the bit resulting in fracture. Advantageously, the point contacts 11 can be regulated either (a) to reside a distance along a radius, bisecting the sector, of at least one-half the sector radius but within 0.01875–0.0312 inch, to induce edge chipping, or (b) to reside a distance along a radius bisecting the sector, of at least the sector radius and no less than 0.0625 inches, to induce a center break indicative of bend strength of the bit.

If testing at high temperature conditions is desired, the constraining means for the curvilinear members, means 42 (curvilinear members), means 20 for restraining the bit, and the load applying means 32 are all constituted of heat fused ceramic such as silicon nitride or silicon carbide.

Preferably the apparatus may have any one of the following features: (a) a load applying means comprised of a substantially spherical member contacting the opposite end surface at substantially the center thereof, (b) the member constraining means and members constituted of heat fused ceramic to permit the apparatus to carry out testing under high temperature conditions, (c) the members of substantially equal radii related to the size of the tool bit for defining the tangential contacts, and (d) the members comprised of metallic ball bearings provided with a dimensional tolerance of plus or minus 0.0001 inch, a surface finish of about 1.5 (arithmetic average) microinches, and a hardness of at least 60 on the Rockwell C scale.

EXAMPLES

To illustrate the advantages of the above test apparatus and method, several ceramic tool bits were tested. Each of the tool bits had a substantially square configuration according to designation SNG 434. Such designation means the bit had a squareness or side dimension of ½ inch, a thickness of 3/16, and a corner radius of 4/64. Each bit was comprised of hot pressed $Si_3N_4$ material. To locate stress points properly, a cavity 15 was arranged with four ball bearings (11–14) in the manner as illustrated in FIG. 1. Each ball bearing first had a diameter of 0.375 and the load sphere 23 had a diameter of 0.5 inch. The bearings had a surface finish typical of standard steel bearings, and a dimensional tolerance of plus or minus 0.0001 inch. The ball bearings and tool bits were placed in a constraining position as shown in FIG. 1 with the tangential contact points forming a square configuration and meeting the tool bit at points spaced just inside the corners of the tool bit by a predetermined dimension of 0.0625 inch. Upon applying a load force, the bend strength of the bit was determined. The percent failure values were plotted logarithmically against stress to render a Weibull plot (see FIG. 4). Weibull plotting is a statistical approach to analytically viewing test data. The angle of slope will be indicative of the scatter of the test data. Weibull plotting is particularly helpful with ceramics which may tend to have considerable scatter, indicative of nonuniform material. The technique for using Weibull plotting is explained in a book entitled *Statistical Design and Analysis of Engineering Experiments*, by Charles Lipson and Narendra Sheth, McGraw Hill Publishing Company, 1973, pages 36–44.

In FIG. 4, the plot line 43 represents test results (percent failure versus stress) for the actual tool bits, and plot lines 42 and 41 represent, respectively, a number of cross-ground modulus of rupture (MOR) test specimens of the same material and a number of longitudinally ground, A sized, MOR bars of the same material. A size here means width ¾ inch, height ⅛ inch, and length 1¼ inches. The reliability of direct testing, using the method and apparatus of this invention, is clearly evident since all of plot 43 falls between the two plots 42 and 41 for two different extremes of specimen bar grinding for the same material.

We claim:

1. A method of directly testing the strength of a prism shaped ceramic cutting tool bit, said bit having parallelogram sides bounded by opposed polygonal end surfaces greater in dimension than the height of any of said sides, the corners of the polygonal end surfaces each being defined by a curved sector surface of predetermined radius, comprising the steps of:
   (a) locating a series of constrained members selected as to size and butted together so that such members make tangential point contact with one bit end surface supported on said members, said point contact being located along a radius bisecting a corner curved sector surface, said point contact being spaced from said curved sector surface a distance of at least one-half said curved sector surface radius but within the dimensional range of 0.01875–0.0312 inches;
   (b) laterally restraining said bit supported on said member; and
   (c) applying a centralized load to the opposite end surface to induce stress in said bit resulting in edge chipping fracture.

2. The method as in claim 1, in which said bit has square shaped end surfaces except for said corners and said series of members is comprised of four hardened ball bearings, each making point contact with said one end surface along diagonals of said end surface.

3. A method of directly testing the strength of a prism shaped ceramic cutting tool bit, said bit having parallogram sides bounded by opposed polygonal end surfaces greater in dimension than the height of any of said sides, the corners of the polygonal end surfaces each being defined by a curved sector surface of predetermined radius, comprising the steps of:
   (a) locating a series of constrained members selected as to size and butting together so that such members have tangential point contact with one bit end surface supported on said members, said point contact being located along a radius bisecting a corner curved sector surface, said location being spaced from the curved sector surface a distance of at least the sector radius and no less than 0.0625 inches;
   (b) laterally restraining said bit supported on said members; and
   (c) applying a centralized load to the opposite end surface to induce stress in said bit resulting in a center break indicative of bend strength.

4. An apparatus for directly testing the strength of a prism shaped ceramic cutting tool bit, said bit having parallogram sides bounded by opposed polygonal end surfaces greater in dimension than the height of any of said sides, the corners of said polygonal end surfaces each being defined by a curved sector surface of predetermined radius, said apparatus comprising:
   (a) means providing three or more abutting and constrained curvilinear members each stationed to make tangential point contact with one end surface of said bit when supportedly located on said members, said point contact being located along a radius bisecting a corner curved sector surface, said location being spaced from the curved sector surface a distance of at least one-half said curved sector surface radius but within the dimensional range of 0.01875–0.0312 inches, said members being sized to regulate the positioning of one contact, each to a corner in close proximity for each curved sector surface of said one end surface;
   (b) means restraining said bit in said located position on said member; and
   (c) load applying means for applying a force to substantially the center of the opposite end surface, which force is effective to induce an edge chipping fracture in said tool bit.

5. The apparatus as in claim 4, in which the corner sectors have a radius in the range of 0.031–0.250.

6. The apparatus as in claim 4, in which means are provided for constraining said members, said constraining means and members being constituted of heat fused ceramic to permit said apparatus to carry out testing under high temperature conditions.

7. The apparatus as in claim 4, in which said members have substantially equal radii related to the size of said tool bit for defining said tangential contacts.

8. The apparatus as in claim 4, in which said members are comprised of metallic ball bearings having a dimensional tolerance of plus or minus 0.0001 inch, a surface finish of about 1.5 (arithmetic average) microinches, and a hardness of at least 60 on the Rockwell C scale.

* * * * *